(12) United States Patent
Dijkstra et al.

(10) Patent No.: US 7,950,284 B2
(45) Date of Patent: May 31, 2011

(54) INSPECTION DEVICE AND METHOD FOR INSPECTION

(75) Inventors: Frederik Hendrik Dijkstra, Oudenbosch (NL); Paul André De Jong, Vlaardingen (NL); Herman Jozef Moolenaar, Rotterdam (NL); Thomas Theodorus A. Van Overbeek, Delft (NL)

(73) Assignee: Röntgen Technische Dienst B.V., NC Rotterdam (NL)

( * ) Notice: Subject to any disclaimer, the term of this patent is extended or adjusted under 35 U.S.C. 154(b) by 139 days.

(21) Appl. No.: 12/232,468

(22) Filed: Sep. 17, 2008

(65) Prior Publication Data

US 2009/0084184 A1    Apr. 2, 2009

Related U.S. Application Data

(63) Continuation of application No. PCT/NL2008/050605, filed on Sep. 15, 2008.

(60) Provisional application No. 60/960,166, filed on Sep. 18, 2007.

(51) Int. Cl.
*G01N 29/04* (2006.01)

(52) U.S. Cl. .................. 73/623; 73/600; 73/602; 73/626

(58) Field of Classification Search .................. 73/866.5, 73/602, 579, 597, 623, 598, 625, 629, 600, 73/622, 641, 599, 626
See application file for complete search history.

(56) References Cited

U.S. PATENT DOCUMENTS

| | | | |
|---|---|---|---|
| 4,601,024 A | 7/1986 | Broding | |
| 4,805,156 A | 2/1989 | Attali et al. | |
| 5,591,912 A | 1/1997 | Spisak et al. | |
| 5,834,871 A * | 11/1998 | Puskas | 310/316.02 |
| 5,932,807 A | 8/1999 | Mallart | |
| 6,474,165 B1 | 11/2002 | Harper et al. | |
| 6,684,706 B2 * | 2/2004 | Knight et al. | 73/623 |
| 6,959,603 B2 * | 11/2005 | Knight et al. | 73/623 |
| 7,354,556 B2 * | 4/2008 | Perkins | 422/128 |
| 7,565,252 B2 * | 7/2009 | Kim et al. | 702/35 |
| 7,628,075 B2 * | 12/2009 | Kennedy et al. | 73/628 |

FOREIGN PATENT DOCUMENTS

JP    2001-50937    2/2001

* cited by examiner

*Primary Examiner* — Jacques M Saint Surin (57) ABSTRACT

Device for ultrasonic inspection of a wall of a pipeline that encloses a fluidum. The device is arranged to be moveable along a device axis through the pipeline along a longitudinal direction of the pipeline. The device is provided with electronic means, a body, a transmitting transducer and at least two receiving transducers, mutually spaced apart in a first transducer array along an array direction that is directed substantially parallel to the device axis. The electronic means are arranged to operate the transmitting transducer for transmitting a first ultrasonic signal to propagate through the fluidum to reach the wall, and to operate the at least two receiving transducers for receiving a second ultrasonic signal, which originates from the first ultrasonic signal after it is modified by the wall, according to a tandem method. The at least two receiving transducers are operated for receiving substantially simultaneously.

39 Claims, 5 Drawing Sheets

INSPECTION DEVICE AND METHOD FOR INSPECTION

This is a continuation of PCT/NL08/050605 filed Sept. 15, 2008 and published in English, claiming benefit of U.S. provisional application number 60/960,166, filed Sept. 18, 2007.

The invention relates to a device for ultrasonic inspection of a wall of a pipeline that encloses a fluidum, the device being arranged to be moveable along a device axis through the pipeline along a longitudinal direction of the pipeline. The invention further provides a method for ultrasonic inspection of a wall of a pipeline that encloses a fluidum.

A known device for inspecting a pipeline is for example described in U.S. Pat. No. 5,932,807. Such a known device can be used for inspecting a wall of the pipeline, from within the pipeline. In use the known device is transported through the pipeline, and during movement the ultrasonic transducers repeatedly transmit and receive ultrasonic signals for inspection. The known device described in U.S. Pat. No. 5,932,807 operates according to Time-of-Flight Diffraction (ToFD), where diffractions from a defect in the pipeline wall, for example a fracture, are detected.

In practice, some fractures are difficult to detect using ToFD. For example, when a fracture is only marginally opened, transmission through the fracture can be largely unaffected by the fracture and as a result diffractions are difficult to detect. Leaving fractures undetected can lead to further damage of the pipeline, such as breakage of the pipeline. This can cause pollution of the environment, loss of large quantities of oil, and/or danger for persons, animals, plants and/or goods and equipment in the vicinity of the pipeline. In addition to such inspection quality, total inspection time of the pipeline is also important. For example, operating the device at a limited travel velocity through the pipeline can lead to a relatively large inspection time that can be very costly. For example, when inspecting an oil production pipeline, inspection time goes at the expense of oil production. As a result, a compromise between inspection quality and inspection time in general is used.

It is an object of the invention to provide an improved device for inspecting a wall of a pipeline. It is another object of the invention to provide a device for inspecting a wall of a pipeline that can enable an improved balance between inspection quality and inspection time.

The invention provides a device for ultrasonic inspection of a wall of a pipeline that encloses a fluidum, the device being arranged to be moveable along a device axis through the pipeline along a longitudinal direction of the pipeline, the device being provided with electronic means, a body, a transmitting transducer and at least two receiving transducers, which transmitting and receiving transducers are attached to the body and are mutually spaced apart in a first transducer array along an array direction that is directed substantially parallel to the device axis, wherein the electronic means are arranged to, preferably repeatedly, operate the transmitting transducer for transmitting a first ultrasonic signal to propagate through the fluidum to reach the wall, and to, preferably repeatedly, operate the at least two receiving transducers for receiving a second ultrasonic signal, which originates from the first ultrasonic signal after it is modified by the wall, according to a tandem method, wherein the at least two receiving transducers are operated for receiving substantially simultaneously. In the tandem method, modifying of the first ultrasonic signal by the wall preferably includes ultrasonic reflection at the defect. In this way a measurement time of a tandem array scan by using the first array of ultrasonic transducers according to the tandem method can be decreased. In particular, in this way fractures can be measured that are oriented in a direction transverse to the longitudinal direction. Such fractures can occur in pipelines for example as a result of fatigue from repeated loading. Also, a total amount of transducers of the at least two receiving transducers does not limit the measurement time, in particular the measurement time stays substantially equal if the total amount of transducers is increased, since the total amount of transducers are operated for receiving substantially simultaneously. In this way the resolution of the tandem array scan of the wall can be increased without negatively affecting the measurement time. Another advantage of the device is that in general it yields smaller amounts of data than other methods, in particular the ToFD method, without giving in on measurement quality. Yet another advantage of using the device according to the invention compared with using a ToFD-based device is that it enables more sensitive detection that is based on a change in an ultrasonic signal as a result of reflection from the fracture instead of transmission through the fracture.

In a preferred embodiment of the device, the device is provided with a second transmitting transducer in the first transducer array, wherein the electronic means are arranged to operate the second transmitting transducer according to a pulse-echo method. Preferably, the device is further provided with a third transmitting transducer in the first transducer array, wherein the electronic means are arranged to operate the third transmitting transducer according to a transmission method. More preferably, the first transmitting transducer forms at least one of the second and third transmitting transducer. It is clear that the second transmitting transducer is also operated for receiving. In this way relatively small fractures, that extend from the inner or outer surface of the pipeline into the pipeline, can be detected substantially simultaneously with carrying out the tandem array scan.

In a more preferred embodiment of the device, the device is further provided with additional transducer arrays being similar to the first transducer array, wherein the first transducer array and the additional transducer arrays are distributed along a circumferential direction of the device that is oriented substantially perpendicular to the device axis.

Preferably, a spacing of a pair of neighbouring transducer arrays of the first transducer array and/or the additional transducer arrays is substantially the same for each pair of neighbouring transducer arrays of the first transducer array and/or the additional transducer arrays along the circumferential direction of the device. In this way, the tandem array scan can be carried out around the whole circumference of the pipe at a location of the device in the pipeline, and an optimal coverage along the circumferential direction can be achieved.

More preferably, the first transducer array and the additional transducer arrays form a plurality of transducer array groups, each including substantially the same number of arrays, wherein the electronic means are arranged for simultaneously operating transducer arrays in at least two transducer array groups. In this way a total measurement time needed for the tandem array scans along the whole circumference can be decreased, and a travel velocity of the device can be increased, thus decreasing inspection time.

In an embodiment, the electronic means are arranged for combining, such as stacking, a plurality of second ultrasonic signals that are modified by one and the same defect in the wall and that are received during different tandem scans by different transducers of the at least two receiving transducers, for obtaining information about a presence and/or a size of the one and the same defect. Different tandem scans for example succeed each other in time. Different transducers are preferably separate from each other.

In an embodiment, the different tandem scans directly follow each other and the different transducers of the at least two receiving transducers are neighbouring transducers. Transducers can be considered to be neighbouring in case there is no other transducer present between these transducers. In this embodiment, an optimal spatial and temporal resolution can be obtained.

The invention further provides a method for ultrasonic inspection of a wall of a pipeline that encloses a fluidum, using an inspection device provided with a transmitting transducer and at least two receiving transducers, which transmitting and receiving transducers are spaced apart in a first transducer array along an array direction that is substantially parallel with a longitudinal direction of the pipeline, including a) moving the device through the pipeline in the longitudinal direction of the pipeline, and b) operating the transmitting transducer for transmitting a first ultrasonic signal to propagate through the fluidum and reach the wall, and operating the at least two receiving transducers for receiving a second ultrasonic signal that originates from the first ultrasonic signal after it is modified by the wall, according to a tandem method, wherein the at least two receiving transducers are operated for receiving substantially simultaneously.

In an embodiment, the method includes combining, such as stacking, a plurality of second ultrasonic signals that are modified by one and the same defect in the wall and that are received during different tandem scans by different transducers of the at least two receiving transducers, for obtaining information about a size of the one and same defect. Such combining can include correcting for time differences between the different tandem scans, so that a coherent image of the one and the same defect can be obtained.

Preferably, the method according to the invention includes correcting the second ultrasonic signal using a measured fluidum pressure and/or fluidum temperature in the pipeline, for determining an ultrasonic propagation velocity in the fluidum, and/or using an eccentricity of the device in the pipeline for determining a distance from the device to an inner surface of the pipeline. In this way a good comparison of measurements in different parts of the pipeline can be performed allowing for different temperatures and pressures of the fluidum, which influence a propagation velocity of the first and second ultrasonic signal. In particular, this enables accurate measurements in riser pipelines, for example catenary risers, in particular used off-shore, where temperature and pressure can vary substantially along a vertical direction of the riser pipeline.

The invention will now be described in more detail, in a non-restrictive way, with reference to the accompanying drawing, in which.

Figure 1A:
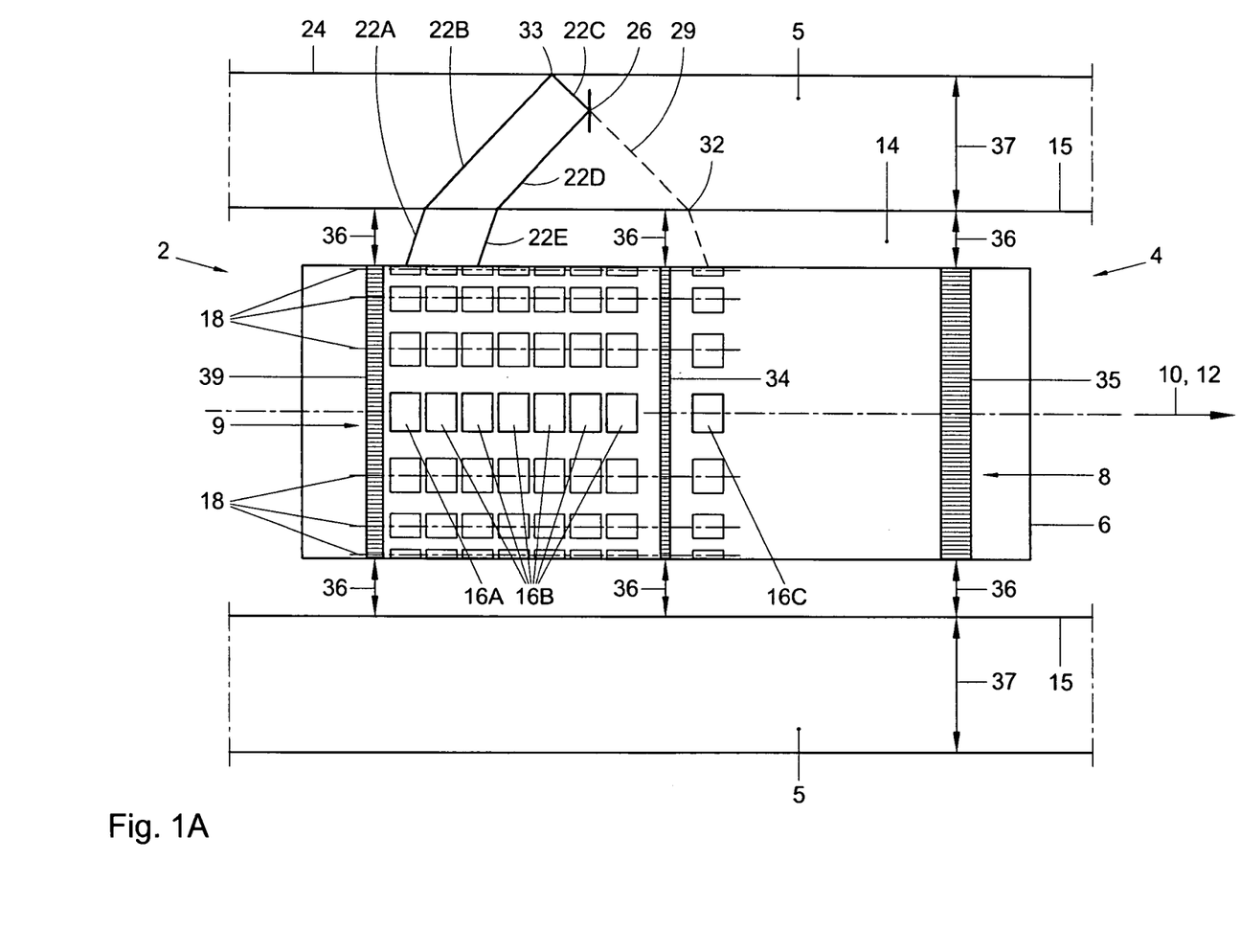
FIG. 1A shows a schematic view of a preferred embodiment of a device according to the invention in a straight pipeline portion.

FIG. 1A shows a schematic view of a preferred embodiment of a device 2 according to the invention, in a straight portion of a pipeline 4 that has a wall 5. The device 2 includes a body 6 and includes a plurality of ultrasonic transducers 8, part of which is shown in FIG. 1A. The device 2 is arranged to be moveable along an imaginary device axis 10 of the device 2, through the pipeline 4 along a longitudinal direction 12 of the pipeline 4. Preferably, the device 2 is arranged to substantially inspect the complete wall of the pipeline 4 through which it moves, with a predetermined spatial and/or temporal inspection resolution. This can be achieved by repeatedly operating the ultrasonic transducers 8. In use of the device in a straight portion of the pipeline 4, the device axis 10 and the longitudinal direction 12 substantially coincide. The pipeline encloses a fluidum 14, for example oil or water that is present in the pipeline 4. The device 2 further includes electronic means (not shown) arranged for operating each one of the plurality of ultrasonic transducers 8 for transmitting and/or receiving an ultrasonic signal. Since it will be clear to someone of ordinary skill in the art how the electronic means operate an ultrasonic transducer for transmitting and/or receiving, this is not explained in detail here. The electronic means can for example be substantially enclosed by the body 6. As a result of transmitting, a first ultrasonic signal can propagate through the fluidum and reach the wall 5. When receiving, a second ultrasonic signal that originates from the first ultrasonic signal and that is modified by the wall, can be received. Such modification can for example be the result of one or more of a reflection at an inner surface 15 of the wall, a reflection at an outer surface 24 of the wall, and transmission through the inner surface 15 of the wall. Alternatively, or additionally, such modification can for example be the result of reflection at, transmission through, or diffraction from a defect in the wall. In this example the modification is the result of reflection at a defect 26 inside the wall, for example a fracture 26. Such a fracture 26 can for example be a fatigue crack as a result of repeated loading, for example bending, of the pipeline 4. The pipeline 4 can for example be a riser pipeline, connected with an offshore oil production platform, for example in a relatively deep sea. The repeated loading can result from swell of the deep sea. In this example the fracture 26 can be oriented in a direction transverse to the longitudinal direction 12.

The plurality of ultrasonic transducers 8 includes a transmitting transducer 16A, receiving transducers 16B, and a transceiving transducer 16C. Herein a transceiving transducer is understood to be operable both as a transmitting transducer and as a receiving transducer. The transmitting transducer 16A, the receiving transducers 16B, and in this example also the transceiving transducer 16C, are mutually spaced apart in a first transducer array 9. The first transducer array 9 has an array direction that is directed substantially parallel to the device axis 10. The plurality of ultrasonic transducers 8 can also include additional transducer arrays similar to the first transducer array 9, indicated by lines 18 in FIG. 1A. Not all of the additional transducer arrays 18 are shown, for clarity.

The electronic means are arranged to operate the transmitting transducer 16A and the receiving transducers 16B according to a tandem method, wherein the transmitting transducer 16A is operated for transmitting, and at least two of the receiving transducers 16B are operated for receiving substantially simultaneously. In the tandem method, the first ultrasonic signal 22A is transmitted by the transmitting transducer 16A. When reaching the wall, the first ultrasonic signal 22A is refracted at the inner surface 15, leading to a third ultrasonic signal 22B. Preferably, the third ultrasonic signal 22B makes an angle of approximately 45 degrees with the axis of symmetry 12 of the pipeline 4. The third ultrasonic signal 22B is subsequently reflected at the outer surface 24 of the wall 5, leading to a fourth ultrasonic signal 22C. The fourth ultrasonic signal 22C inside the pipe wall 5 can be modified, for example reflected, at the defect 26. A fifth ultrasonic signal 22D reflected from the defect 26 then propagates to the inner wall 15, where it is refracted, leading to the second ultrasonic signal 22E that is received by one of the receiving transducers 16B. When the fracture 26 is present at another location within the wall 5, the second ultrasonic signal 22E can be substantially received by another one of the receiving transducers 16B. It is thus clear that a location and size of the fracture 26 determines which one of the receiving transducers 16B substantially receives the second ultrasonic signal 22E after reflection of the fourth ultrasonic signal 22C at the fracture 26.

In general, the more the defect 26 is situated towards the outer surface 24, the closer the receiving transducer 16B that detects the second ultrasonic signal 22E is positioned to the transmitting transducer 16A. The more the defect 26 is situated towards the inner surface 15, the further the receiving transducer 16B that detects the second ultrasonic signal 22E is positioned away from the transmitting transducer 16A. Hence, the position of the receiving transducer 16B that detects the second ultrasonic signal 22E with respect to the transmitting transducer 16A is an indication of a radial position of the defect 26 within the wall 5.

The electronic means may be arranged for combining, such as stacking, a plurality of the second ultrasonic signals 22E that are modified by one and the same defect 26 in the wall and that are received during different tandem scans by different transducers of the receiving transducers 16B, for obtaining information about a size of the one and the same defect 26. The different tandem scans may directly follow each other and the different transducers of the receiving transducers 16B may be neighbouring transducers.

Hence, the electronic means are arranged to operate the transmitting transducer 16A for transmitting the first ultrasonic signal 22A to propagate through the fluidum 14 to reach the wall 5, and to operate at least two of the receiving transducers 16B for receiving the second ultrasonic signal 22E, which originates from the first ultrasonic signal after it is modified by the wall 5, according to the tandem method, wherein the at least two receiving transducers are operated for receiving substantially simultaneously.

When no defect 26 is present, the fourth ultrasonic signal 22C will propagate along the dashed line 29 and will be received by the transceiving transducer 16C. Also, when the defect 26 is partly transparent for ultrasonic waves, an ultrasonic signal will be received by the transceiving transducer 16C when the defect 26 is present. The electronic means can be arranged to operate the transducers 16A and 16C in this way according to a transmission method. This can be carried out before, after, or in combination with operating the first transducer array 9 according to the tandem method. For example, the first ultrasonic signal 22A transmitted in order to operate the transducers 16A and 16B according to the tandem method, may also be used to operate the transducers 16A and 16C according to the transmission method.

When another defect, for example a fracture that extends from the inner surface 15 into the wall 5, is present at a location 32 at the inner surface 15, at least part of the fourth ultrasonic signal 22C that propagates along the dashed line 29 will be reflected back along this line. It is clear that then a sixth ultrasonic signal that originates from the fourth ultrasonic signal 22C reaches the transmitting transducer 16A after reflection at the outer surface 24 and refraction at the inner surface 15. The electronic means are for example arranged to receive the sixth ultrasonic signal, after reflection at the defect at the location 32 at the inner surface 15. In this way the transmitting transducer 16A can be operated according to a pulse-echo method.

When another defect, for example a fracture that extends from the outer surface 24 into the wall 5, is present at a location 33 at the outer surface 24, at least part of the third ultrasonic signal 22B will be reflected back along its ray path. It is clear that then a seventh ultrasonic signal that originates from the third ultrasonic signal 22B reaches the transmitting transducer 16A, after refraction at the inner surface 15. The electronic means can also operate the transmitting transducer 16A to receive the seventh ultrasonic signal after reflection at the defect at the location 33 at the outer surface 24. In this way the transceiving transducer 16A can be operated according to a pulse-echo method.

Operating the transmitting transceiver 16A according to the pulse-echo method can be carried out before, after, or in combination with operating the first transducer array 9 according to the tandem method. For example, the first ultrasonic signal 22A transmitted in order to operate the transducers 16A and 16B according to the tandem method, may be used for operating the transceiving transducer 16A according to the pulse-echo method. Alternatively or additionally, the transceiving transducer 16C can also be operated according to a pulse-echo method analogously to the transceiving transducer 16A. Using the transceiving transducer 16A also for at least one of the pulse-echo method and the transmission method enables an increase of detection speed and a decrease of inspection time. The operation of the first transducer array 9 is further illustrated in reference to FIG. 1B.

The first transducer array 9 and the additional transducer arrays 18 are distributed along a circumferential direction of the device (not shown in FIG. 1A but shown in FIG. 2 with reference number 46) that is oriented substantially perpendicular to the device axis 10. For example, the first transducer array 9 and the additional transducer arrays 18 are distributed at regular distances along the circumferential direction of the device 2. This means that a spacing of neighbouring transducer arrays of a set of transducer arrays comprising the first transducer array 9 and/or the additional transducer arrays 18 is substantially the same for each pair of neighbouring transducer arrays of the set of transducer arrays comprising the first transducer array 9 and/or the additional transducer arrays 18 along the circumferential direction of the device 2. Preferably, the electronic means are arranged to operate the additional transducer arrays 18 similarly to the first transducer array 9. The first transducer array 9 and the additional transducer arrays 18 can for example form a plurality of transducer array groups, each group including substantially the same number of arrays, wherein the electronic means are arranged for simultaneously operating transducer arrays in at least two transducer array groups. In this way a total measurement time needed for tandem array scans of the first transducer array 9 and the additional transducer arrays 18 can be reduced, and a travel velocity of the device can be increased, thus decreasing inspection time. The number of transducer array groups can for example be such that transducers arrays in neighbouring transducer array groups that are operated simultaneously by the electronic means, do not substantially hinder each other, at least not to a level that is difficult to correct.

A distance from the transducers 16A, 16B, and 16C of the first transducer array 9 and the additional transducer arrays 18 to the inner surface 15 of the wall 5 is for example 3 cm, or for example 2 cm, or for example a value in a range from 1 to 10 cm.

The plurality of ultrasonic transducers 8 can also include a second transducer array 34 of transducers. The transducers of this second transducer array 34 are, for example regularly, spaced apart along the circumferential direction of the device. The electronic means are in this example arranged to operate the transducers of the second transducer array 34 according to a pulse-echo method in order to inspect the inner surface 15 of the wall 5. In this way, defects in the inner surface of the wall 5 can be detected. Such defects can for example be a result of corrosion and/or erosion of the inner surface 15. As a result of corrosion and/or erosion, a first distance 36 from the device to the wall can be increased. By measuring a propagation time through the fluidum 14 of an eighth ultrasonic signal, in this preferred embodiment transmitted by a transceiving transducer of the second transducer array 34, and the second ultrasonic signal that originates from the eighth ultrasonic signal after it is modified by the wall, in this example reflected at the inner surface 15 of the wall 5, the first distance 36 can be determined using a known and/or predetermined ultrasonic signal propagation velocity in the fluidum 14. Preferably, the second transducer array 34 is positioned halfway a length of the body of the device measured along the array direction. In this way, the device axis 10 and the longitudinal direction 12 of the pipeline will be substantially parallel to each other at a position of the second transducer array 34, also in a bended portion of the pipeline. As a result, the eighth ultrasonic signal will still be reflected substantially perpendicularly to the inner surface 15 and will be received by the transducer of the second transducer array 34, also in the bended portion of the pipeline. The ultrasonic transducers of the second transducer array 34 have a transmitting and receiving surface that is for example substantially flat and have for example a substantially circular circumference, with a diameter of for example 3 mm.

The plurality of ultrasonic transducers can further include a third transducer array 35 of transducers. The transducers of the third transducer array 35 are spaced apart, for example regularly, along the circumferential direction of the device. The electronic means can be arranged to operate the transducers of the third transducer array 35 according to a pulse-echo method in order to inspect the outer surface 24 of the wall 5, for example to determine a second distance 37 being substantially equal to a thickness of the wall 5. Additionally, or alternatively, the third transducer array 35 can be arranged to determine the first distance 36 from the device 2 to the inner surface 15 of the wall 5. An example of the third transducer array 35 will be described in reference to FIGS. 2 and 4.

The device 2 can further include means for determining eccentricity of the device, i.e. the eccentricity of the device in a transverse sectional view of the pipeline. In this example, the means for determining the eccentricity of the device are arranged for measuring a distance from the device 2 to the wall 5 at least two pair of distinct positions. One pair of the at least two pair of distinct positions is located near a first end of the device and another pair of the at least two pair of distinct positions is located near a second end of the device, the first and second end of the device being opposite ends of the device along the device axis. In this preferred embodiment, the means for determining the eccentricity of the device 2 can include further transducers 39 included by the plurality of ultrasonic transducers 8. These further transducers 39 are for example arranged in a fourth transducer array in the circumferential direction of the device and are operated by the electronic means to measure the first distance 36 to the inner wall 15. Together with the first distance 36 determined by using transducers of the third transducer array 35, the eccentricity of the device in the pipeline 4 can be determined, by using mathematical methods known as such to the person skilled in the art.

Figure 3:
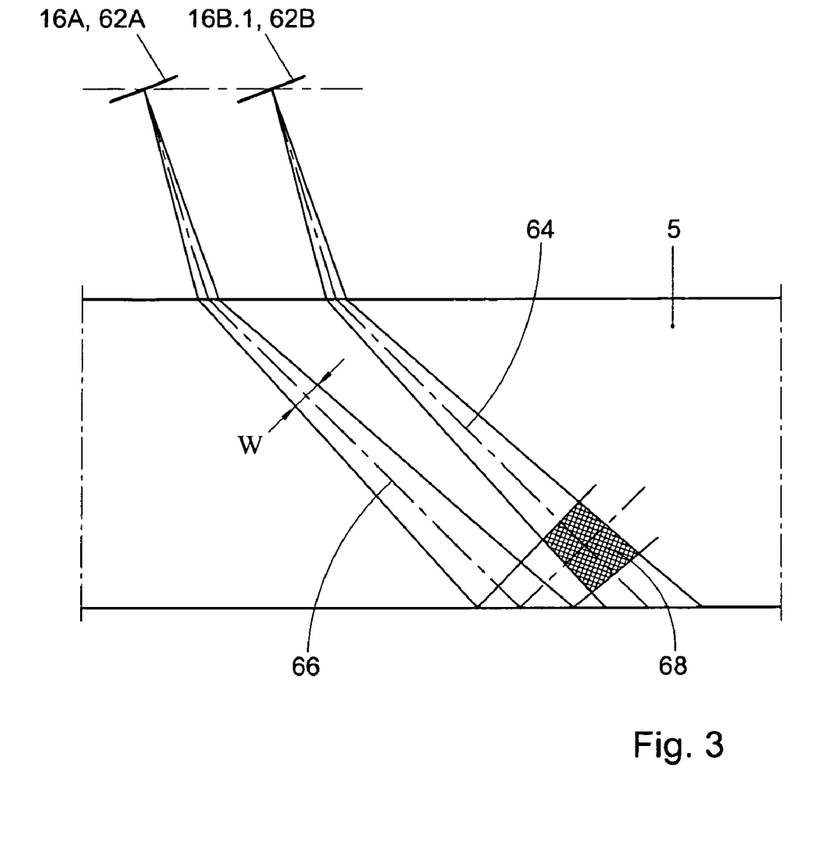
FIG. 3 shows a transmitting transducer-receiving transducer combination that consists of ultrasonic transducers in the preferred embodiment of FIGS. 1A and 1B.

Preferably, the travel velocity of the device 2 in use is such that a travel distance of the device 2 during a scan time interval, from a first tandem scan start to a second tandem scan start that directly follows the first tandem scan start, is much smaller, for example three or more times smaller, or for example five or more times smaller, than a first dimension of the receiving surface of one of the receiving transducers 16B and/or than a second dimension of an intersection area of a first ultrasonic beam 64 received via the receiving surface 62B and a second ultrasonic beam 66 transmitted via the transmitting surface 62A (FIG. 3). The first dimension may be a diameter, and the second dimension may be measured along the longitudinal direction.

Figure 1B:
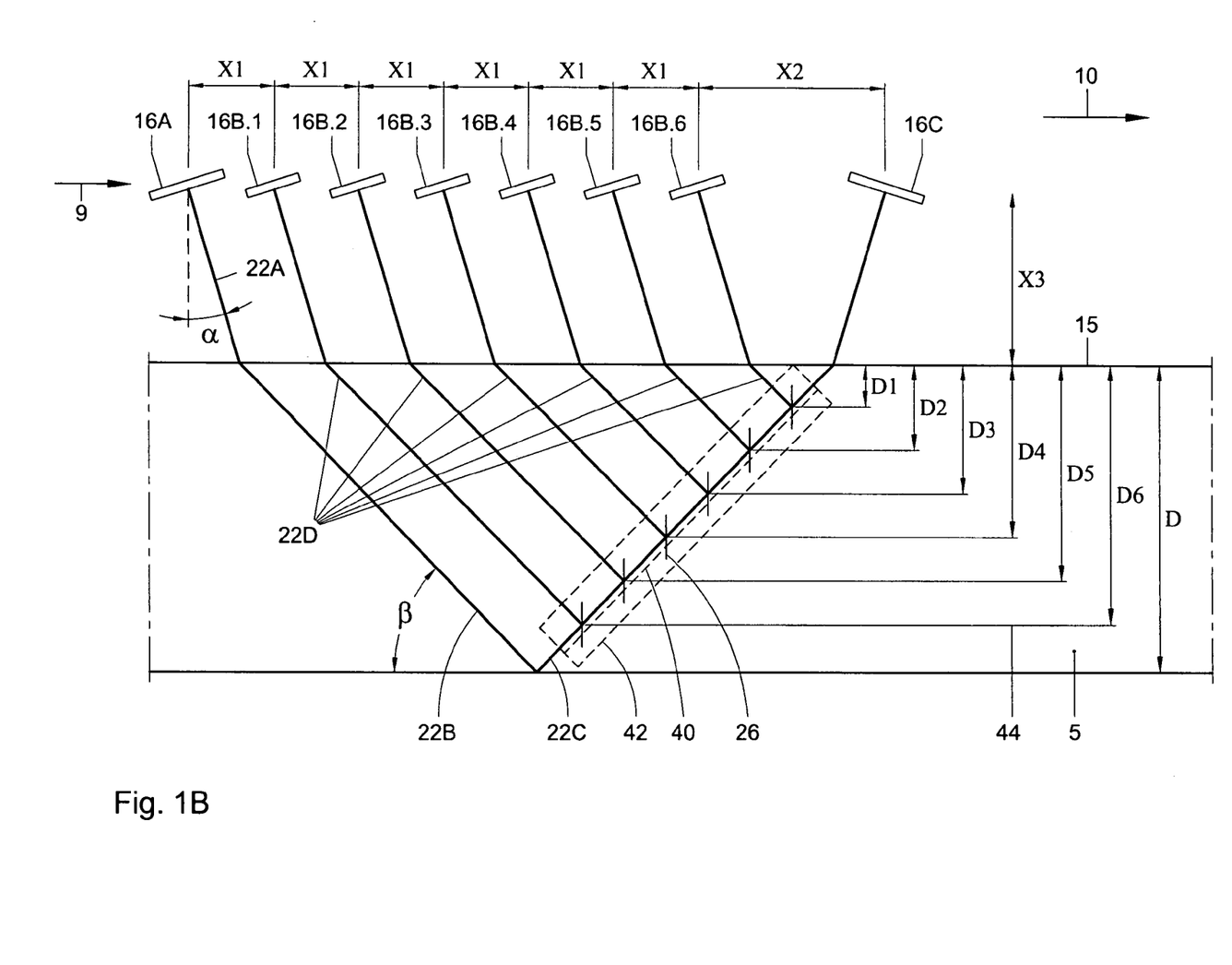
FIG. 1B shows a detailed view of ultrasonic transducers in the preferred embodiment of FIG. 1A, and a wall.

FIG. 1B shows a detailed view of the transducers 16A, 16B, and 16C in the preferred embodiment of FIG. 1A, and the wall 5. The transducers 16A and 16B are regularly spaced apart in the array direction, with a spacing $x_1$. This means for example that the spacing $x_1$ between a pair of neighbouring transducers of the transducers 16A,B is substantially the same for each pair of neighbouring transducers of the transducers 16A,B. A spacing $x_2$ from the receiving transducer 16B.6 to the transceiving transducer 16C may be different from the spacing $x_1$. FIG. 1B shows a number of fractures 26 and a number of distinct ray paths of the fifth ultrasonic signals 22D. In particular, a total ray path of the ultrasonic signals 22A-E, from the transmitting transducer 16A to one of the receiving transducers 16B.1-6, is of substantially equal length for each of the receiving transducers 16B.1-6. At least two transducers, in this example the receiving transducers 16B.1-6, are preferably operated for receiving substantially simultaneously. In this way a fracture that is present at the dashed line 40, for example one of the fractures 26, will cause one of the reflected fifth ultrasonic signals 22D to be generated. If the fractures 26 are partly transparent for ultrasonic waves so that not all ultrasonic energy is reflected, more than one of the fractures 26 can reflect the ultrasonic waves.

FIG. 1B also shows a number of depth zones, a center of which is indicated by lines 44. The first transducer array 9 is arranged so that each of the receiving transducers 16B.i inspects a different depth zone 44, a center of which is located at a depth D1, D2, D3, D4, D4, D5, or D6, measured from the inner surface 15. The number of depth zones 44 is related to the number of receiving transducers 16B, and is substantially unrelated to a measurement time of a tandem array scan, by using the first transducer array 9 according to the tandem method. This is because only one transmitting transducer 16A is used, and reception of ultrasonic signals from all depth zones 44 takes place substantially simultaneously.

A detection zone 42 around the dashed line 40, with a length substantially equal to the dashed line 40, can be defined. A reflection from a defect 26 in the detection zone 42 is received by at least one of the receiving transducers 16B.1-6, after refraction at the inner surface 15. A width of the detection zone 42 depends on a beam width of the fourth ultrasonic signal 22C, which in turn depends on a beam width of the first ultrasonic signal 22A. A beam width of the fifth ultrasonic signal 22D that is, after refraction at the inner surface 15, received by the receiving transducers 16B, is such that beams of neighbouring fifth ultrasonic signals 22D may at least partially overlap. In this way a reflection from a defect 26 inside the detection zone 42 is received by at least one of the receiving transducers 16B. Preferably, the overlap between neighbouring beams of the neighbouring fifth ultrasonic signals 22D is such that they have a dip of preferably maximum 6 dB going from the center of one of the neighbouring beams transversely to the neighbouring beams to a position halfway a separation between the neighbouring beams. This leads to an economic use of transducers and improves scan speed while maintaining sufficient accuracy.

The device 2 is for example arranged to detect all fractures 26 in the wall 5 with thickness D that have a fracture height larger than a predetermined minimum fracture height, related to the predetermined spatial resolution. In this case, the number of receiving transducers 16B can for example be substantially equal to the thickness D divided by a height of one of the depth zones 44, which height is directed transverse to the longitudinal direction.

The spacing of neighbouring transducers of the receiving transducers 16B is for example such that an ultrasonic signal reflected at a defect inside the wall is received by at least one transducer of the at least two receiving transducers of the first transducer array 9. The receiving transducers 16B are for example spaced apart at regular intervals, which in this example means that the spacing between a pair of neighbouring transducers of the receiving transducers 16B is substantially the same for each pair of neighbouring transducers of the receiving transducers 16B. In this preferred embodiment the first transducer array 9 includes six receiving transducers 16B. The first transducer array 9 may also include for example two, three, four, five, seven, eight, nine, ten, eleven, or twelve receiving transducers 16B, or more than twelve receiving transducers 16B.

In use of the device 2, in a preferred method according to the invention, it is moved through the pipeline and scanning is carried out simultaneously by operating the transducers 8 by the electronic means. During movement, the detection zone 42 moves with the device 2. The scan time interval may for example be substantially equal to a dimension of the detection zone 42 along the longitudinal direction 12 divided by the travel velocity of the body 6 through the pipeline 4. In this way the detection speed is substantially maximised while still inspecting the complete wall 5 of the pipeline 4 through which the device 2 moves.

The device 2 can be arranged to be able to stop at a location along the pipeline 4, for example at welds between pipes of the pipeline 4. Approaches similar to methods in the field of pipeline automated ultrasonic testing (pipeline AUT) that are known as such to the person skilled in the art can for example be implemented in the device 2 and can be used for inspection of the welds, but now from within the pipeline 4. For that reason, the device 2 may be provided with extendable elements arranged to establish mechanical contact of at least one transducer of the plurality of ultrasonic transducers 8 with the inner surface of the wall 5. In this case, separate and preferably different probes can be used for each depth zone 44, and also larger crystals and focusing lenses or phased arrays if required, resulting in narrower beams and smaller depth zones 44. Also other techniques requiring contact of the ultrasonic transducers and the inner wall 15 (for example using creeping waves and/or high-resolution ToFD) can be implemented in the device 2. In this way a relative accurate measurement can be performed.

Figure 2:
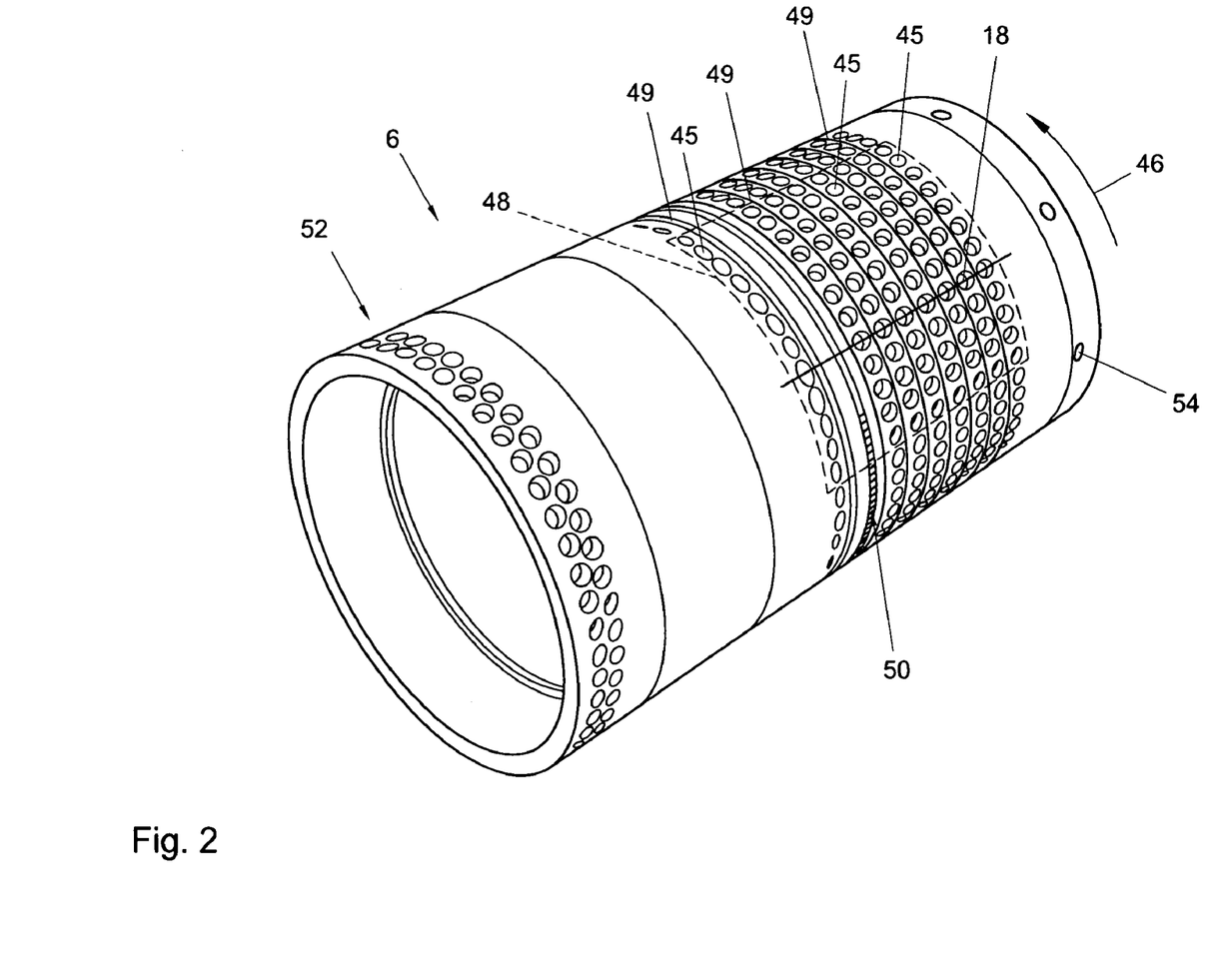
FIG. 2 shows a body, which is provided with cavities each of which is arranged to take up an ultrasonic transducer.

FIG. 2 shows a body 6, which is provided with first cavities 45. The first cavities 45 are in particular arranged to take up the first transducer array 9 and the additional transducer arrays 18. The first cavities 45 are for example arranged to take up fifty additional transducer arrays 18 in addition to the first transducer array 9, in case the inner diameter of the pipeline 4 has a diameter substantially equal to 12 inch (30 cm) and the stand-off distance, equal to the first distance 36, is for example near or equal to 3 cm. Preferably, the body 6 is arranged to take up, by means of the first cavities 45, the first transducer array 9 and the additional transducer arrays 18 at regular distances along the circumferential direction 46 of the device.

The first cavities 45 in the area enclosed by the dashed line 48 can be arranged to take up a transducer array group. Such a transducer array group consists for example of twelve or thirteen transducer arrays, of the first transducer array 9 and the additional transducer arrays 18. The device 2 can be arranged to measure simultaneously in at least two transducer array groups, for example in four transducer array groups, or alternatively in three, five, six, seven, eight, nine, ten, eleven, twelve, or more than twelve transducer array groups. In this way the scan speed can be further increased. In particular, transducer arrays of the first and additional transducer arrays 9, 18 that measure simultaneously, are spaced apart along the circumferential direction 46 of the device at mutual intervals of substantially 90 degrees or a multiple thereof. In this way arrays of ultrasonic transducers that measure simultaneously do not substantially hinder each other. In this preferred embodiment, the transmitting transducer 16A, the receiving transducers 16B.i, and the transducers 16C each form tandem rings 49.

The body 6 is arranged to take up the second transducer array 34 in second cavities 50. The body 6 is further provided with third cavities 52, arranged to take up the third transducer array 35. The body is further provided with fourth cavities 54 arranged to take up the further transducers 39. A shape of the body is such that ultrasonic reflection coming from the body does not substantially hinder the ultrasonic measurements. This is especially relevant for transducers of the first transducer array 9 or the additional transducer arrays similar to the first transducer array 9.

In general, the body 6 may be of modular design. Thereto the body 6 may comprise a number of mutually coupled rings. One of the rings may comprise the second cavities 50, another one of the rings may comprise the third cavities 52, and/or yet another one of the rings may comprise the fourth cavities 54. The first cavities 45 may be comprised by only one of the rings, or by a group of the rings. For example, one ring of the group of the rings may comprise the cavities 45 for taking up the receiving transducers 16B.i, another ring of the group of the rings may comprise the cavities 45 for taking up the transmitting transducers 16A, and/or yet another ring of the group of the rings may comprise the cavities 45 for taking up the transducers 16C. It is also possible that an annular subgroup of receiving transducers 16B.i of the group of receiving transducers 16B.i is comprised by a single ring. Preferably, ultrasonic transducers taken up by one of the rings are operated by the electronic means separately from other ultrasonic transducers not taken up by the one of the rings. Thereto the electronic means may comprise several distinct parts. One of such distinct parts is preferably associated with only the transducers taken up by the one of the rings. Other distinct parts may be individually associated with transducers taken up by other rings in a similar way. This may hold for all distinct parts. Preferably, the one of the distinct parts is mounted inside the one of the rings without exceeding a size of the one of the rings in the longitudinal direction 12. Other distinct parts may individually be mounted inside other rings in a similar way. This may hold for all distinct parts. It may be clear however that the electronic means may still be arranged for time-synchronised operation of the ultrasonic transducers taken op by the group of the rings and/or by the number of mutually coupled rings. Such a modular design greatly enhances flexibility concerning a number of used transducers arrays, a number of transducers in the first transducer array, and/or a length of the body 6. Such flexibility for example enables adaption of the number of receiving transducers 16B.i dependent on the wall thickness, or adaption of a length of the device 2 dependent on bend characteristics of the pipeline 4.

FIG. 3 shows a transmitting transducer-receiving transducer combination 60 that consists of the transducers 16A and 16B in the preferred embodiment of FIGS. 1A and 1B. The transmitting transducer 16A has the transmitting surface 62A and the receiving transducers 16B have the receiving surface 62B. The transmitting and receiving surface 62A and 62B are for example substantially flat and have for example a substantially circular circumference. The first ultrasonic beam 64 received via the receiving surface 62B and the second ultrasonic beam 66 transmitted via the transmitting surface 62A intersect at a position 68. Preferably, the first and second ultrasonic beam 64 and 66 have a similar width at the position 68 where the first and second ultrasonic beam 64 and 66 intersect. In order to achieve this, a size, for example a diameter, of the transmitting surface 62A and the receiving surface 62B are substantially different from one another. In this way, a difference in length of a ray path from transducers 16A,B to the position 68 can be compensated for, as beam width increases along a ray path. In particular, the surface 62A is larger than the surface 62B. The surface 62A can for example have a diameter 1.5 to 2 times larger than the surface 62B. For example, the surface 62A has a diameter substantially equal to 10 mm and the surface 62B has a diameter substantially equal to 6 mm.

Figure 4:
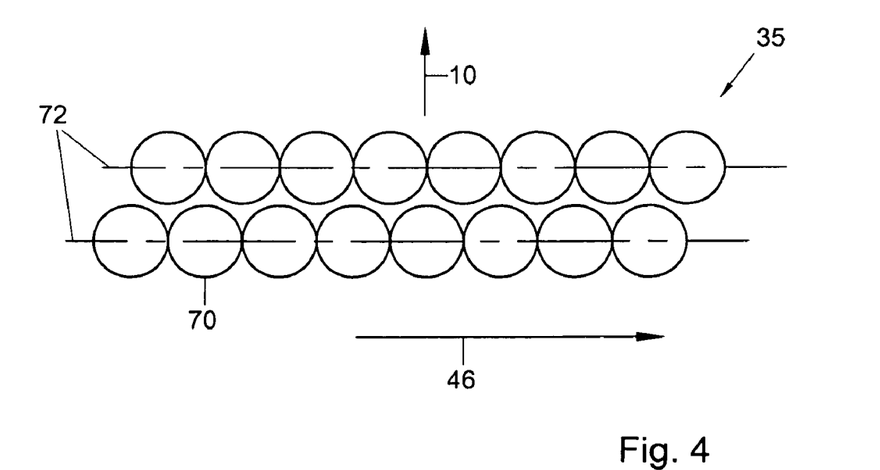
FIG. 4 shows a schematic detail of a part of a third array of ultrasonic transducers, operated according to a pulse-echo method.

FIG. 4 shows a schematic detail of a part of the third transducer array 35. The device axis 10 and the circumferential direction 46 of the device are indicated. The transducers 70 of the third transducer array 35 have a diameter large enough for pulse-echo measurement for inspection of the outer surface 24 of the wall 5. For example, the diameter of the transducers 70 is substantially equal to 10 mm. The transducers 70 can be attached to the body 6 along two interlaced circumferential rings 72. This has the advantage that a larger resolution of inspection along the circumferential direction 46 of the device can be obtained than when using only one circumferential ring 72.

In the preferred method according to the invention, at least one of a fluidum pressure in the pipeline, a fluidum temperature in the pipeline, and the eccentricity of the device in the pipeline are determined, for example all of these. The fluidum temperature and pressure are determined using for example a temperature sensor and a pressure sensor that are attached to the body 6. The eccentricity is for example determined by using the third transducer array 35 and using further ultrasonic transducers 39. Using the determined eccentricity, temperature, and pressure, the propagation times for each scan can be corrected, because propagation velocities of ultrasonic signals depend on temperature and pressure, and distances 36 depend on the eccentricity of the device 2 in the pipeline 4. Mathematical equations, known as such to the person skilled in the art, can be used for such corrections. Such corrections, being an example of processing of the received signals 22E of FIGS. 1A and 1B, may be carried out in-line and/or real-time, for example directly after scanning by using the electronic means, or after scanning is completed in an off-line analysis separate from scanning. In this way, scans at different times can be better combined with each other using a reference temperature and pressure, and zero eccentricity.

The preferred method according to the invention includes moving the device 2 through the pipeline 4 in the longitudinal direction 12 of the pipeline 4. This can be performed by towing the device 2, for example by using a pipeline pig. Such a pipeline pig can be moved in a variety of ways known as such to the person skilled in the art, for example by a pressure difference in the fluidum 14 over the pipeline pig. Also, two or more devices 2 can be moved through the pipeline 4 simultaneously, so that quality of detection is even further improved, and they may be connected by a flexible cord. If an inlet and an outlet location of in the pipeline 4 for the device 2 are mutually adjacent or coinciding, the device 2 may inspect the pipeline during movement away from the inlet and outlet location and also during movement towards the inlet and outlet location.

According to the preferred method of the invention, A-scans obtained by means of the transmitting transducer 16A and receiving transducers 16B when the body 6 is moved to different locations and possibly stopped at such locations, may be stacked so that these stacked A-scans provide defect information over the total thickness of the pipe wall 5 at a certain location.

Figure 5A:
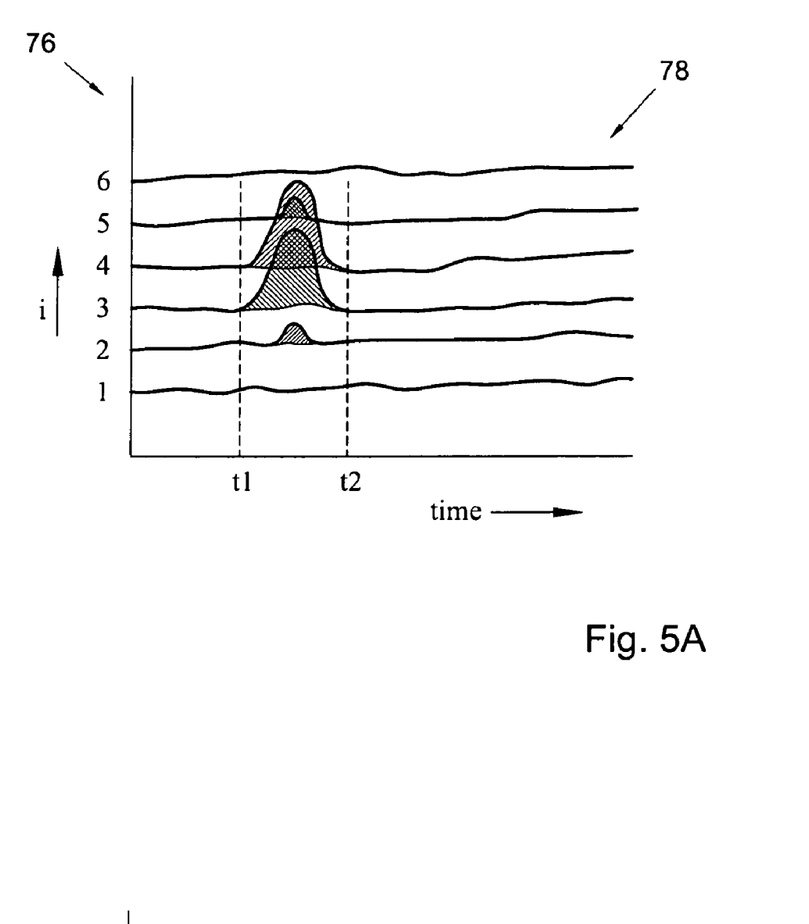
FIG. 5A shows an example of a stacked A-scan that is made in a method according to the invention.

FIG. 5A shows an example of a stacked A-scan 76 that can be made in the preferred method according to the invention. The stacked A-scan 76 of FIG. 5A is formed by stacking A-scans 78 of the second ultrasonic signal 22E in FIGS. 1A and 1B, which originates from the first ultrasonic signal 22A after it is modified by the defect 26, and a number of similar received signals, together forming the plurality of second ultrasonic signals 22E. In particular, all these received signals are modified by the one and the same defect 26 and are received during different tandem scans and by different transducers of the first transducer array 9, for example tandem scans that directly follow each other. In this way, information can be obtained about a size of the one and the same defect. The different transducers of the transducer array 9 may be neighbouring transducers, thus increasing a spatial detection resolution of the preferred method.

From FIGS. 1A and 1B it is clear that when the device 2 moves through the pipeline, different tandem combinations of the transmitting transducer 16A and a receiving transducer 16B.i in different depth zones 44 will not detect a large crack at the same time with the device 2 at the same position in the pipeline 4, but there will be a time difference and a device position difference between the depth zones 44. In the preferred method, this can be corrected by adequate time correction and/or correction for the device position, for example in off-line software or in-line and/or real-time. A suitable time correction algorithm (or, rather, position correction) will be able to visualize the crack in a coherent image as detected by multiple zones, by using for example time corrected stacked A-scans (similar to time-corrected C-scan mapping in pipeline AUT). Position correction is relatively insensitive for deviations in the travel velocity of the device 2. In the example of FIG. 5A, receiving transducers 16B.2-5 detect the fracture 26. The second ultrasonic signal 22E received by receiving transducers 16B.3 and 16B.4 is rather strong, and the second ultrasonic signal 22E received by receiving transducers 16B.2 and 16B.5 is rather weak, but still detectable. By comparing the amplitude of the rather weak and the rather strong signals, an extent of the fracture into a corresponding depth zone 44 may be inferred.

Figure 5B:
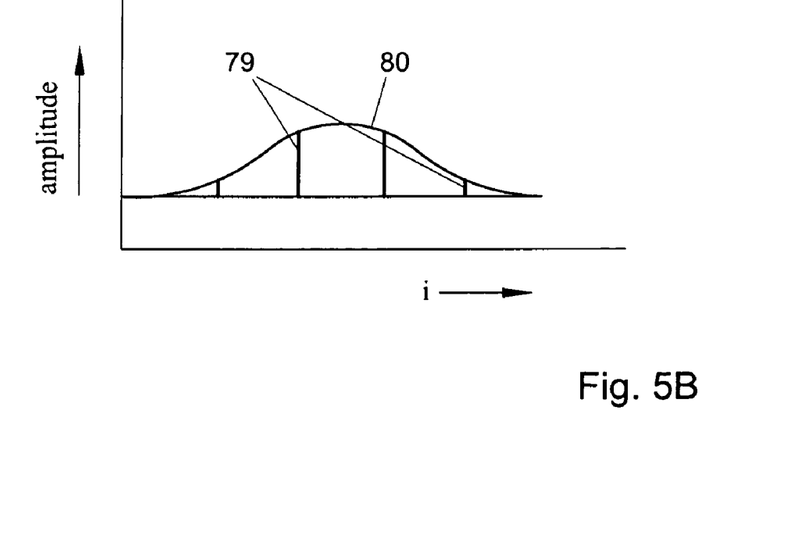
FIG. 5B shows signal amplitudes in a time window.

FIG. 5B shows amplitudes 79 of the second ultrasonic signals 22E of FIG. 5A in a time window t1-t2, as indicated in FIG. 5A. An envelope 80 can be drawn over the signal amplitudes 79. Such an envelope 80 can be used for analysing characteristics of the defect, in particular the fracture 26. A size of the fracture 26 may be inferred from the envelope 80. For example, the fracture height may be related to a width of the envelope 80 at an amplitude equal to half of a maximum amplitude of the envelope 80. Also, an opening of the fracture can be inferred from the envelope 80. In particular, the shape of the envelope 80 can be compared between distinct defects. Additionally or alternatively, defects can be classified based on the envelope 80. The envelope 80 may be compared with a similar envelope measured in a calibration pipe, which includes a defect with a known geometry and size.

The preferred method according to the invention can for example also include determining a location of the device 2 in the pipeline 4 along the longitudinal direction 12. This can for example be performed by using a pinger or a metering wheel and registering each turn of the metering wheel. Additionally or alternatively, this can be performed by identifying a measurement of each weld between neighbouring pipes of the pipeline, and combining this with a known length of the pipes.

It is thus believed that the operation and construction of the present invention will be apparent from the foregoing description. The invention is not limited to any embodiment herein described and, within the purview of the skilled person, modifications are possible which may be considered within the scope of the appended claims. Equally all kinematic inversions are considered inherently disclosed and to be within the scope of the present invention. Expressions such as: "means for . . . " should be read as: "component configured for . . . " or "member constructed to . . . " and should be construed to include equivalents for the structures disclosed. The use of expressions like: "preferably", "preferred", "in particular" etc. is not intended to limit the invention. Features which are not specifically or explicitly described or claimed may be additionally included in the structure according to the present invention without deviating from its scope.

The invention claimed is:

1. A device for ultrasonic inspection of a wall of a pipeline that encloses a fluidum, the device being arranged to be moveable along a device axis through the pipeline along a longitudinal direction of the pipeline, the device being provided with electronic means, a body, a transmitting transducer and at least two receiving transducers, which transmitting and receiving transducers are attached to the body and are each mutually spaced apart in a first transducer array along an array direction that is directed substantially parallel to the device axis, wherein the electronic means are arranged to operate the transmitting transducer for transmitting a first ultrasonic signal to propagate through the fluidum to reach the wall, and to operate the at least two receiving transducers for receiving a second ultrasonic signal, which originates from the first ultrasonic signal after it is modified by the wall, according to a tandem method, wherein the at least two receiving transducers are operated for receiving the second ultrasonic signal substantially simultaneously.

2. The device according to claim 1, wherein the at least two receiving transducers are operated for receiving the second ultrasonic signal after reflection at a defect in the wall.

3. The device according to claim 1, wherein a spacing of a pair of neighbouring transducers of the at least two receiving transducers is substantially the same for each pair of neighbouring transducers of the at least two receiving transducers.

4. The device according to claim 1, wherein the first transmitting transducer has a transmitting surface and the at least two receiving transducers each have a receiving surface, wherein a size of the transmitting surface is different from a size of the receiving surface.

5. The device according to claim 4, wherein a first ultrasonic beam received via the receiving surface and a second ultrasonic beam transmitted via the transmitting surface have a similar width at a position where the first and second ultrasonic beam intersect.

6. The device according to claim 1, further provided with a second transmitting transducer in the first transducer array, wherein the electronic means are arranged to operate the second transmitting transducer according to a pulse-echo method.

7. The device according to claim 6, wherein the second transmitting transducer is attached to the body at an angle with the array direction so that a transmitted ultrasonic signal propagates inside the wall at an angle of substantially 45 degrees with the device axis.

8. The device according to claim 6, wherein the first transmitting transducer forms at least one of the second and third transmitting transducer.

9. The device according to claim 1, further provided with a third transmitting transducer in the first transducer array, wherein the electronic means are arranged to operate the third transmitting transducer according to a transmission method.

10. The device according to claim 1, further provided with additional transducer arrays being similar to the first transducer array, wherein the first transducer array and the additional transducer arrays are distributed along a circumferential direction of the device that is oriented substantially perpendicular to the device axis.

11. The device according to claim 10, wherein a spacing of a pair of neighbouring transducer arrays of the first transducer array and/or the additional transducer arrays is substantially the same for each pair of neighbouring transducer arrays of the first transducer array and/or the additional transducer arrays along the circumferential direction of the device.

12. The device according to claim 10, wherein the first transducer array and the additional transducer arrays form a plurality of transducer array groups, each including substantially the same number of arrays, wherein the electronic means are arranged for operating transducer arrays in at least two transducer array groups simultaneously.

13. The device according to claim 1, wherein the electronic means are arranged for combining, such as stacking, a plurality of second ultrasonic signals that are modified by one and the same defect in the wall and that are received during different tandem scans by different transducers of the at least two receiving transducers, for obtaining information about a size of the one and the same defect.

14. The device according to claim 13, wherein the different tandem scans directly follow each other and the different transducers of the at least two receiving transducers are neighbouring transducers.

15. The device according to claim 1, further provided with a second transducer array including ultrasonic transducers that are spaced apart along the circumferential direction of the device, wherein the electronic means are arranged to operate the ultrasonic transducers of the second transducer array according to a pulse-echo method in order to inspect the inner surface of the wall.

16. The device according to claim 15, wherein the second transducer array is positioned substantially halfway a length of the body of the device along the array direction.

17. The device according to claim 1, further provided with a third transducer array including ultrasonic transducers that are spaced apart along the circumferential direction of the device, wherein the electronic means are arranged to operate the ultrasonic transducers of the third transducer array according to a pulse-echo method in order to inspect the outer surface of the wall.

18. The device according to claim 1, including means for determining an eccentricity of the device arranged for measuring a distance from the device to the wall at least two pair of distinct positions, wherein one pair of the at least two pair of distinct positions is located near a first end of the device and another pair of the at least two pair of distinct positions is located near a second end of the device, the first and second end of the device being opposite ends of the device along the device axis.

19. The device according to claim 18, wherein the means for determining eccentricity of the device include further ultrasonic transducers and the electronic means are arranged for operating the further ultrasonic transducers according to a pulse-echo method.

20. The device according to claim 1, including at least one of a first sensor for determining a pressure of the fluidum and a second sensor for determining a temperature of the fluidum.

21. The device according to claim 1, further provided with extendable elements arranged to establish mechanical contact of a number of ultrasonic transducers of at least one of the first, second, and third transducer arrays with the inner surface of the wall.

22. A method for ultrasonic inspection of a wall of a pipeline that encloses a fluidum, using an inspection device provided with a transmitting transducer and at least two receiving transducers, which transmitting and receiving transducers are each spaced apart in a first transducer array along an array direction that is substantially parallel with a longitudinal direction of the pipeline, including:
 a) moving the device through the pipeline in the longitudinal direction of the pipeline; and
 b) operating the transmitting transducer for transmitting a first ultrasonic signal to propagate through the fluidum and reach the wall, and operating the at least two receiving transducers for receiving a second ultrasonic signal that originates from the first ultrasonic signal after it is modified by the wall, according to a tandem method, wherein the at least two receiving transducers are operated for receiving the second ultrasonic signal substantially simultaneously.

23. The method according to claim 22, including combining, such as stacking, a plurality of second ultrasonic signals that are modified by one and the same defect in the wall and that are received during different tandem scans by different transducers of the at least two receiving transducers, for obtaining information about a size of the one and the same defect.

24. The method according to claim 23, including making a stacked A-scan of the plurality of second ultrasonic signals.

25. The method according to claim 22, wherein the different tandem scans directly follow each other and the different transducers of the at least two receiving transducers are neighbouring transducers.

26. The method according to claim 22, further including operating a second transmitting transducer of the first transducer array according to a pulse-echo method.

27. The method according to claim 22, further including operating a third transmitting transducer of the first transducer array according to a transmission method.

28. The method according to claim 26, wherein the first transmitting transducer forms at least one of the first and second transmitting transducer.

29. The method according to claim 22, further including operating additional transducer arrays similarly to operating the first transducer array, wherein the first transducer array and the additional transducer arrays are spaced apart along a circumferential direction of the device that is oriented perpendicular to the array direction.

30. The method according to claim 29, wherein a spacing of a pair of neighbouring transducer arrays of the first transducer array and/or the additional transducer arrays is substantially the same for each pair of neighbouring transducer arrays of the first transducer array and/or the additional transducer arrays along the circumferential direction of the device.

31. The method according to claim 29, wherein two or more transducer arrays, of the first transducer array and the additional transducer arrays, are operated simultaneously.

32. The method according to claim 22, further including operating ultrasonic transducers of a second transducer array according to a pulse-echo method in order to inspect an inner surface of the wall, wherein the ultrasonic transducers of the second transducer array are spaced apart along the circumferential direction of the device.

33. The method according to claim 22, further including operating ultrasonic transducers of a third transducer array according to a pulse-echo method in order to inspect an outer surface of the wall, wherein the ultrasonic transducers of the third transducer array are spaced apart along the circumferential direction of the device.

34. The method according to claim 22, further including determining an eccentricity of the device inside the pipeline by determining a distance from the device to the inner surface of the wall near ends of the device that are mutually opposite along the device axis.

35. The method according to claim 22, including measuring at least one of a pressure of the fluidum and a temperature of the fluidum at a position adjacent to the device.

36. The method according to claim 35, including correcting the second ultrasonic signal using a measured fluidum pressure and/or fluidum temperature in the pipeline, for determining an ultrasonic propagation velocity in the fluidum, and/or using an eccentricity of the device in the pipeline for determining a distance from the device to an inner surface of the pipeline.

37. The method according to claim 22, including stopping the device and carrying out an ultrasonic inspection measurement wherein a number of ultrasonic transducers of at least one of the first, second, and third transducer array, make direct mechanical contact with the wall.

38. The method according to claim 22, further including determining a location of the device in the pipeline along the longitudinal direction.

39. The method according to claim 22, wherein the device is a device for ultrasonic inspection of a wall of a pipeline that encloses a fluidum, the device being arranged to be moveable along a device axis through the pipeline along a longitudinal direction of the pipeline, the device being provided with electronic means, a body, a transmitting transducer and at least two receiving transducers, which transmitting and receiving transducers are attached to the body and are mutually spaced apart in a first transducer array along an array direction that is directed substantially parallel to the device axis, wherein the electronic means are arranged to operate the transmitting transducer for transmitting a first ultrasonic signal to propagate through the fluidum to reach the wall, and to operate the at least two receiving transducers for receiving a second ultrasonic signal, which originates from the first ultrasonic signal after it is modified by the wall, according to a tandem method, wherein the at least two receiving transducers are operated for receiving substantially simultaneously.

* * * * *